United States Patent [19]

Höchstetter

[11] Patent Number: 5,095,103

[45] Date of Patent: Mar. 10, 1992

[54] POLYCYCLIC AROMATIC AZACYCLIC COMPOUNDS USEFUL IN DYEING

[75] Inventor: Hans Höchstetter, Düsseldorf, Fed. Rep. of Germany

[73] Assignee: Bayer Aktiengesellschaft, Leverkusen, Fed. Rep. of Germany

[21] Appl. No.: 626,606

[22] Filed: Dec. 12, 1990

[30] Foreign Application Priority Data

Dec. 23, 1989 [DE] Fed. Rep. of Germany ....... 3942893

[51] Int. Cl.$^5$ .......................................... C07D 471/22
[52] U.S. Cl. ..................... 534/752; 544/14; 544/95; 544/233; 544/245; 540/556; 546/27; 546/28; 546/37; 546/48
[58] Field of Search ............ 540/556; 544/95, 14, 544/233, 245; 546/27, 28, 37, 48; 534/752

[56] References Cited

U.S. PATENT DOCUMENTS 4,486,587 12/1984 Seybold ................................ 546/28

OTHER PUBLICATIONS

Ferrier et al., J. Chem. Soc., pp. 3513-3515 (1960).

*Primary Examiner*—Bernard Dentz
*Attorney, Agent, or Firm*—Sprung Horn Kramer & Woods

[57] ABSTRACT

Heterocyclic compounds of the formula

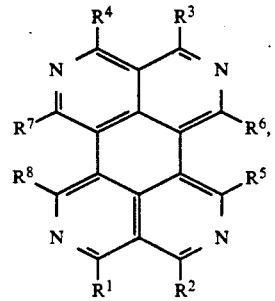

with the substituent meanings given in the description, and derivatives thereof are suitable for dyeing and pigmenting the most diverse substrates.

18 Claims, No Drawings

POLYCYCLIC AROMATIC AZACYCLIC COMPOUNDS USEFUL IN DYEING

The invention relates to heterocyclic compounds of the formula

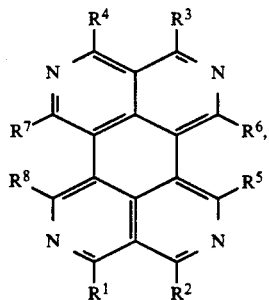

wherein $R^1$ to $R^8$ denote H, halogen, alkyl, cycloalkyl, aralkyl, aryl, a heterocyclic radical, $NR^9R^{10}$, $OR^9$ or $SR^9$, wherein $R^9$ and $R^{10}$ denote H, alkyl, cycloalkyl, aralkyl, aryl or a heterocyclic radical, or the radicals $R^1$ and $R^2$, and $R^3$ and $R^4$, and furthermore $R^5$ and $R^6$, and $R^7$ and $R^8$ together can form components of fused-on carbocyclic or heterocyclic 5-, 6- or 7-membered rings.

Halogen preferably represents Cl, Br or F.

The radicals $R^1$ to $R^{10}$ can have the above meaning independently of one another.

The alkyl, cycloalkyl, aralkyl, aryl and heterocyclic radicals can contain the customary substituents.

Alkyl preferably represents $C_1$–$C_{18}$-alkyl, in particular $C_1$–$C_4$-alkyl. Cycloalkyl preferably represents $C_3$–$C_7$-cycloalkyl, in particular cyclohexyl or cyclopentyl. Possible substituents of the alkyl and cycloalkyl radicals are, for example: halogen, such as Cl, Br or F, $OCOR^{11}$, $OR^{11}$, $SR^{11}$, $NR^{12}R^{13}$, $OCONR^{12}R^{13}$, $COOR^{11}$, $NR^{12}COR^{11}$, $NR^{12}COOR^{11}$, $CONR^{12}R^{13}$, CN, $SO_2R^{11}$, $COR^{11}$, $SO_2OR^{11}$, $-N=N-R^{14}$ or $SO_2NR^{12}R^{13}$.

Particularly preferred alkyl and cycloalkyl radicals for $R^1$ to $R^8$ are those which carry a carbanion-stabilizing group, such as CN, $COOR^{11}$, $CONR^{12}R^{13}$, $SO_2R^{11}$ or $-N=N-R^{14}$, in the α-position.

The radicals $R^{11}$ to $R^{14}$ have the meanings given below.

Aralkyl represents, in particular, phenyl- or naphthyl-$C_1$–$C_4$-alkyl, it being possible for the alkyl carbon atoms to be substituted as described above for alkyl and for the aryl radicals to be substituted as described below for aryl.

Aryl preferably represents those carbocyclic aromatic radicals which contain 1, 2, 3 or 4, in particular 1 or 2, rings, such as phenyl, diphenyl or naphthyl.

Heterocyclic radicals are preferably those heteroaromatic radicals which contain 1, 2, 3 or 4, in particular 1 or 2, five- six- or seven-membered rings, at least one of which preferably contains 1, 2 or 3, preferably 1 or 2, heteroatoms from the series comprising O, N and S. Examples of heterocyclic radicals which may be mentioned are: pyridyl, pyrimidyl, pyrazinyl, triazinyl, furoyl, pyrrolyl, thiophenyl, quinolyl, coumarinyl, benzofuranyl, benzimidazolyl, benzoxazolyl, dibenzofuranyl, benzothiophenyl, dibenzothiophenyl, indolyl, carbazolyl, pyrazolyl, imidazolyl, oxazolyl, isoxazolyl, thiazolyl, indazolyl, benzothiazolyl, pyridazinyl, cinnolyl, quinazolyl, quinoxalyl, phthalazinyl, phthalazinedionyl, phthalimidyl, chromonyl, naphtholactamyl, quinolonyl, ortho-sulphobenzoic acid imidyl, maleimidyl, naphtharidinyl, benzimidazolonyl, benzoxazolonyl, benzothiazolonyl, benzothiazothionyl, quinazolonyl, quinoxalonyl, phthalazonyl, dioxopyrimidinyl, pyridonyl, isoquinolonyl, isoquinolinyl, isothiazolyl, benzisoxazolyl, benzisothiazolyl, indazolonyl, acridinyl, acridonyl, quinazolinedionyl, quinoxalinedionyl, benzoxazinedionyl, benzoxazinonyl and naphthalimidyl.

The aryl and heterocyclic radicals can be substituted for example, by halogen, such as chlorine, bromine and fluorine, CN, $OR^{11}$, $SR^{11}$, $OCOR^{11}$, $OCONR^{12}R^{13}$, $NR^{12}R^{13}$, $NR^{12}COR^{11}$, $NR^{12}COOR^{11}$, $COR^{11}$, $COOR^{11}$, $CONR^{12}R^{13}$, $SO_2R^{11}$, $SO_2NR^{12}R^{13}$, $-N=N-R^{14}$ or $R^{15}$.

$R^{15}$ designates optionally substituted alkyl, preferably $C_1$–$C_{18}$-alkyl, in particular $C_1$–$C_4$-alkyl, or optionally substituted cycloalkyl, preferably $C_3$–$C_7$-cycloalkyl, in particular cyclohexyl or cyclopentyl.

Substituents of the alkyl and cycloalkyl radicals $R^{15}$ can be the same as are described above in the case where $R^1$ to $R^8$ are alkyl or cycloalkyl.

$R^{11}$, $R^{12}$ and $R^{13}$ designate hydrogen, optionally substituted alkyl, in particular $C_1$–$C_{18}$-alkyl, preferably $C_1$–$C_4$-alkyl, optionally substituted cycloalkyl, in particular cyclohexyl or cyclopentyl, optionally substituted aralkyl, in particular phenyl- or naphthyl-$C_1$–$C_4$-alkyl, optionally substituted aryl, in particular phenyl or naphthyl, or an optionally substituted heterocyclic radical, in particular the radical of a five- or six-membered heterocyclic ring having 1, 2 or 3 heteroatoms from the series comprising O, N, S, onto which a benzene ring can be fused.

The alkyl and cycloalkyl radicals $R^{11}$, $R^{12}$ and $R^{13}$ can be substituted, for example, by Cl, Br, F, CN, mono-$C_1$–$C_4$-alkylamino, di-$C_1$–$C_4$-alkylamino, phenyl or naphthyl, which can be substituted by Cl, Br, F, $C_1$–$C_6$-alkyl and $C_1$–$C_6$-alkoxy, or by heterocyclic radicals of a 5- or 6-membered heterocyclic ring system having 1 or 2 heteroatoms from the series comprising O, N and S, onto which a benzene ring can be fused.

$R^{12}$ and $R^{13}$ together, including the N atom, can also form a 5- or 6-membered heterocyclic ring, for example a morpholine, piperidine or phthalimide ring. The aryl and aralkyl radicals $R^{11}$, $R^{12}$ and $R^{13}$ can be substituted, for example, by Cl, Br, F, $C_1$–$C_{18}$-alkyl, preferably $C_1$–$C_4$-alkyl, or by $C_1$–$C_{18}$-alkoxy, preferably $C_1$–$C_4$-alkoxy.

$R^{14}$ designates the radical of a coupling component, preferably a coupling component of the benzene, naphthalene, acetoacetatearylide, pyrazole or pyridone series, or a phenyl radical which is optionally substituted by Cl, Br, F, $C_1$–$C_{18}$-alkyl, preferably $C_1$–$C_4$-alkyl, or $C_1$–$C_{18}$-alkoxy, preferably $C_1$–$C_4$-alkoxy. If adjacent pairs of radicals such as $R^1$-$R^2$, $R^3$-$R^4$, $R^5$-$R^6$, or $R^7$-$R^8$ are components of five-, six- or seven-membered carbo- or heterocyclic rings fused onto the tetraazaperylene system, these adjacent radicals $-R^1$-$R^2-$ and the like can represent the following bridging units:

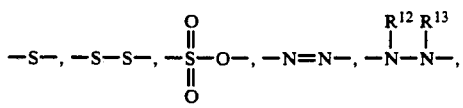

-continued

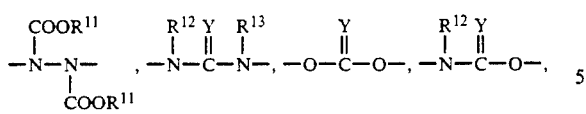

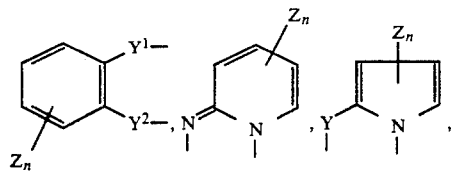

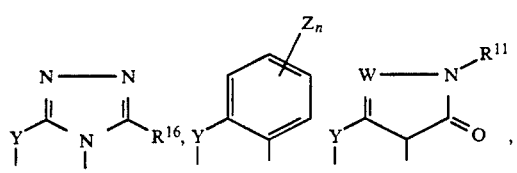

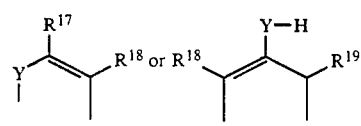

In this list:

$R^{11}$, $R^{12}$ and $R^{13}$ have the meanings described above,

Y, $Y^1$ and $Y^2$ denote O, S, $NR^{12}$ or $NR^{13}$ and

Z denotes $OR^{11}$, $NR^{12}R^{13}$, $SR^{11}$, $COOR^{11}$, CN, Br, Cl, F, $CONR^{12}R^{13}$, $SO_2R^{11}$, $SO_2OR^{11}$, $SO_2NR^{12}R^{13}$, $-N=N-R^{14}$, $R^{15}$, $OCOR^{11}$, $NR^{12}COR^{11}$ or $COR^{11}$.

The index n on the substituent Z can represent 0, 1, 2 or 3. $R^{14}$ and $R^{15}$ have the abovementioned meanings.

$R^{16}$ can represent H or Z,

W can represents $=N-$ or

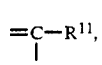

$R^{17}$ represents an optionally substituted aryl or hetaryl radical, which can be substituted as described above for $R^1$=aryl or hetaryl.

$R^{18}$=CN, $COOR^{11}$ or $COR^{11}$ and $R^{19}$=CN, $COOR^{11}$, $COR^{11}$, $SO_2R^{11}$, $COR^{11}$ or $CONR^{12}R^{13}$.

In $R^{18}$ and $R^{19}$, $R^{11}$ to $R^{13}$ have the meanings described above.

One or more rings can be fused onto the tetraazaperylene system of I, and those systems having two or four fused-on rings are preferred.

Combinations of the bridging units listed above are also possible.

Compounds which are preferred in the context of formula I correspond to the formula

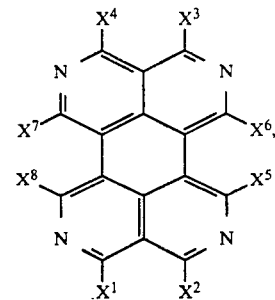

wherein $X^1$ to $X^8$ can be identical or different and represent halogen atoms, such as Br, Cl or F.

The compound IIa in which $X^1$ to $X^8$ represents chlorine is particularly preferred in the context of formula II.

Compounds which are furthermore preferred in the context of formula I are those of the formula

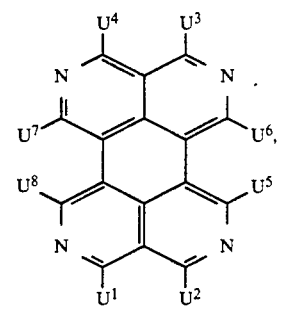

wherein $U^1$ to $U^8$ can be identical or different from one another and can represent $OR^9$, $SR^9$ or $NR^9R^{10}$. $R^9$ and $R^{10}$ have the abovementioned meanings.

Compounds which are particularly preferred in the context of formula I are those of the formula

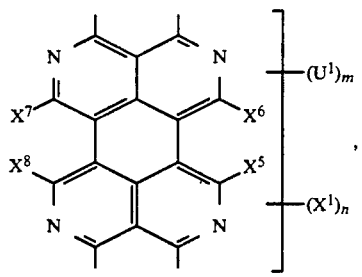

wherein $U^1$ represents identical or different radicals $OR^9$, $SR^9$ or $NR^9R^{10}$; $X^1$ to $X^8$ are identical or different and represent F, Cl or Br and m and n denote 1–4, wherein m+n=4.

Compounds which are preferred in the context of formula IV are those of the formula

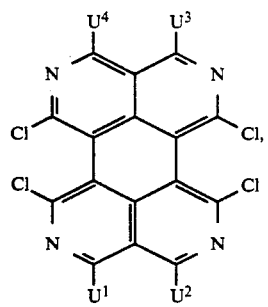

V with the abovementioned meanings for $U^1$ to $U^4$.

Compounds which are preferred in the context of formula V are compounds Va in which $U^1$ to $U^4$ are identical or different from one another and represent the formula

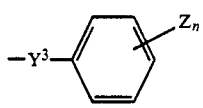

Z has the abovementioned meanings and the index n can represent 0, 1, 2 or 3. $Y^3$ represents O, S or NH, it being possible in the latter case for the compounds V to be present in various tautomeric forms.

Compounds which are furthermore preferred in the context of formula I are those of the formula

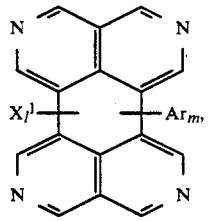

VI wherein $X^1$ has the abovementioned meaning and Ar represents an optionally substituted aromatic or heterocyclic radical such as is described above in more detail for $R^1$.

The indices l and m can assume values between 0 and 8, and their sum must be 8.

Adjacent groups Ar can also be components of a single fused aromatic system.

Compounds which are furthermore preferred in the context of formula I are those of the formula

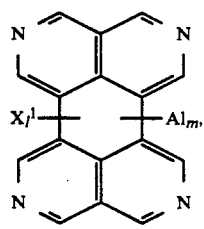

VII where $X^1$ has the abovementioned meaning and Al represents an optionally substituted alkyl, cycloalkyl or aralkyl radical such as described above in more detail for $R^1$.

The same meanings as described for formula VI apply to the indices l and m.

Alkyl, cycloalkyl and aralkyl radicals which are preferred for Al in formula VII are those which carry a carbanion-stabilizing group, such as CN, $COOR^{11}$, $CONR^{12}R^{13}$, $COR^{11}$, $SO_2R^{11}$ or $—N=N—R^{14}$, where the radicals $R^{11}$ to $R^{14}$ have the abovementioned meanings, in the α-position (linking position to the pentacyclic radical).

Compounds which are furthermore preferred in the context of formula I are those of the formula

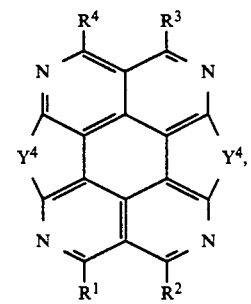

VIII wherein $R^1$ to $R^4$ have the meanings described above and $—Y^4—$ can represent $—S—$, $—S—S—$, $—N=N—$,

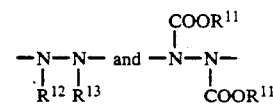

$R^{11}$ to $R^{14}$ have the abovementioned meanings.

Compounds which are preferred in the context of formula VIII are those of the formula

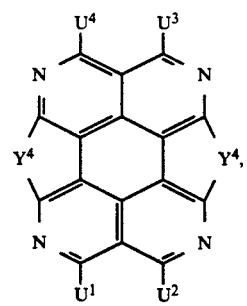

IX with the meanings described above for $U^1$ to $U^4$ and $—Y^4—$;

Compounds which are preferred in the context of formula IX are compounds IXa in which $—Y^4—$ represents $—S—$.

Compounds which are particularly preferred in the context of formula VIII are those of the formula

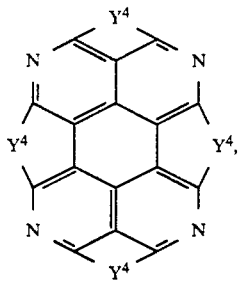
VIII with the meanings described above for —Y⁴—, but where —Y⁴— may not be a constituent of a four-membered ring.

Compounds which are furthermore preferred in the context of formula I are those of the formula

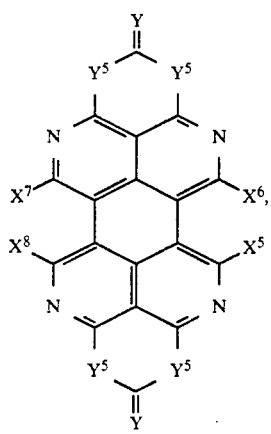
XI wherein $Y^5$ has the meanings O, $NR^{12}$ or Y and $X^5$ to $X^8$ have the meanings described above.

Compounds which are preferred in the context of formula XI are those of the formula XII, in which $X^5$ to $X^8$ represents chlorine and $Y^5$ represents NH.

Compounds which are furthermore preferred in the context of formula I are those of the formula

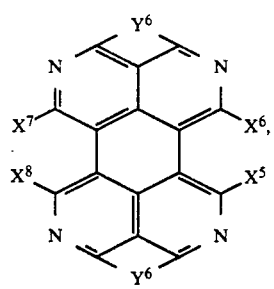
XIII wherein $X^5$ to $X^8$ have the meanings described above and —Y⁶— can represent the following bridging units:

(a): 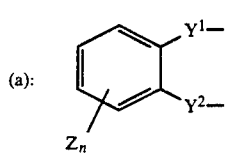

(b): 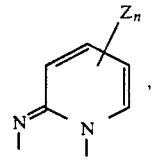

(c): 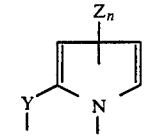

(d): 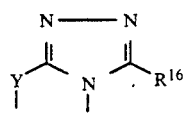

(e): 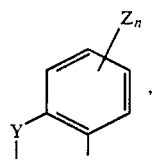

(f): 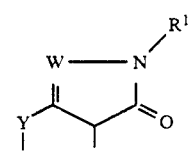

(g): 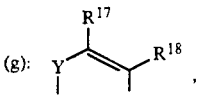

(h): 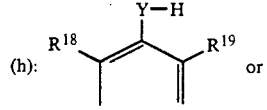 or (i): —S—S—

W, Y, $Y^1$, $Y^2$, $Z_n$, $R^{11}$ and $R^{16}$ to $R^{19}$ have the meanings given above. Since these are unsymmetric bridging units, XIII can be present as a mixture of two isomers. Several tautomeric forms can furthermore exist with certain bridging units.

Compounds which are preferred in the context of formula XIII are those of the formula XIVa

-continued

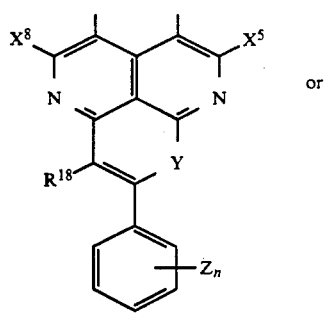 or

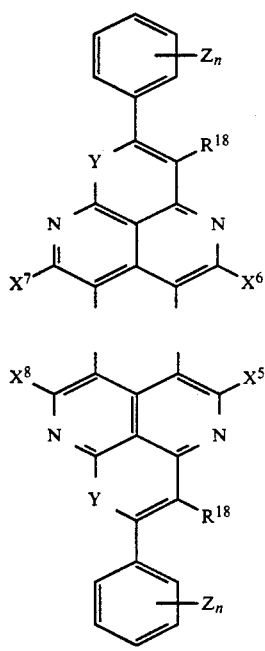

with the abovementioned meanings for $Z_n$, Y, $R^{18}$ and $X^5$ to $X^8$.

Compounds which are furthermore preferred in the context of formula XIII are those which, in one of the possible tautomeric forms, correspond to the formulae XVa
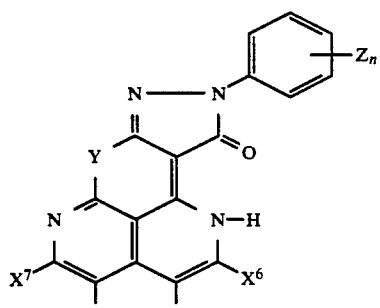

-continued

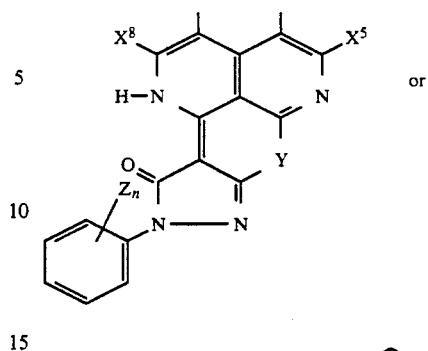 or

XIVb

XVb
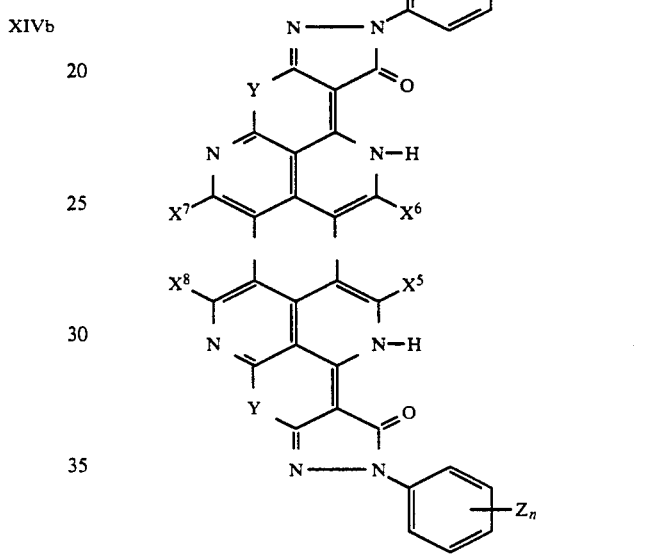

The substituents $Z_n$, Y and $X^5$ to $X^8$ have the meanings described above.

Compounds which are furthermore preferred in the context of formula I are those of the formula XVI
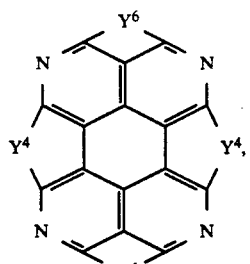

with the meanings described above for $Y^4$ and $Y^6$.

The oxidation of

XVII
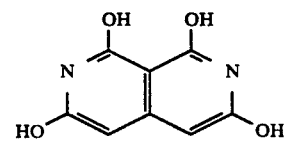

described in J. Chem. Soc. 1960, p. 3513 et seq., gives a pentacyclic radical of the probable structure

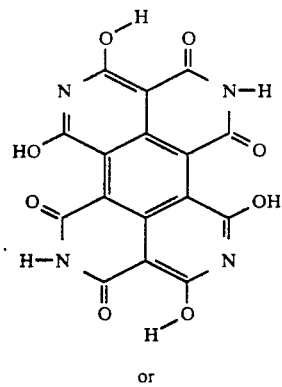

XVIIIa or

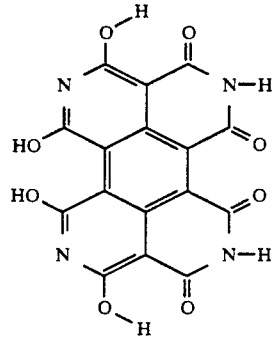

XVIIIb or of one of the possible tautomers with the symmetry of XVIIIa ($C_{2h}$) or XVIIIb ($C_{2v}$), for example

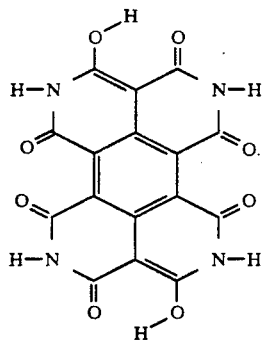

XIX

Compounds of the type II are prepared by reacting the compound XVIII with halogenating agents, such as $PBr_5$, $PCl_5$ or $POCl_3$, at temperatures 120° C. and 240° C., preferably between 140° C. and 160° C., if appropriate in the presence of inert solvents, such as nitrobenzene or o-dichlorobenzene.

If appropriate, the reaction must be carried out under pressure in an autoclave. The stoichiometry must be calculated so that the halogenating agent can supply at least 10 halogen atoms per molecule of XVIII under the reaction conditions. This reaction is formally reductive halogenation which proceeds via a decahalogen derivative of XVIII. The compounds of type II are brown-orange to brown-red solids which are soluble in nonpolar solvents.

Compounds of type III are obtained by reacting compounds of the type II with nucleophiles $U^1$—H to $U^8$—H at temperatures of 20° C. to 260° C., preferably 60° C. to 150° C., if appropriate in inert solvents, such as toluene or o-dichlorobenzene, and if appropriate in the presence of acid-binding agents, such as alkali metal carbonates or tertiary amines. The nucleophile U-H can sometimes be an acid-binding agent itself. It is also possible for the salts of the nucleophiles $U^1$—H to $U^8$—H to be employed.

In these substitution reactions, the halogens $X^1$ to $X^8$ in II exhibit a distinctly graduated reactivity. The atoms $X^1$ to $X^4$ can in all cases be replaced under significantly milder conditions (temperature and pressure) than $X^5$ to $X^8$. If these are also be replaced, the reaction must be carried out with a large excess of nucleophile U—H at temperatures above 200° C. and usually under pressure.

Depending on the stoichiometry of the nucleophile U—H employed, the substituents $X^1$ to $X^4$ in II can also be replaced successively, and mono- to tetrasubstitution products IV can thus be obtained, each of which can be isolated if required and if appropriate employed for further reactions with nucleophiles, if appropriate other nucleophiles.

Compounds of type VI can be obtained by reacting compounds of type II with aromatic compounds Ar—H in the context of a Friedel-Crafts acylation in the presence of more than equimolar amounts of a suitable Friedel-Crafts catalyst, such as, for example, $AlCl_3$. This reaction is carried out at temperatures between 100° C. and 250° C., preferably between 140° C. and 200° C., and if appropriate an inert solvent may be present.

Depending on the reaction conditions, mixtures of type VI are obtained, and if the energy conditions are adequate peraryl compounds VI can also be obtained.

Compounds of type VI can furthermore be obtained by reacting compounds of type II with aromatic-organometallic compounds, such as phenyllithium or phenylmagnesiumbromide.

Compounds of type VII are obtained by reacting compounds of type II with those alkane derivatives G—$CH_2$—$R^{20}$ which can form carbanions and thus function as carbon nucleophiles. The reaction is carried out in inert solvents, such as, for example, high-boiling, chlorine-free aromatics, in which the salt of a carbanion is first produced from compounds of the type G—$CH_2$—$R^{20}$. After addition of the derivative of II, the mixture is then heated to temperatures between 50° C. and 200° C.

The radical G in G—$CH_2$—$R^{20}$ represents carbanion-stabilizing radicals, such as CN, $COOR^{11}$, $CONR^{12}R^{13}$, $COR^{11}$, $SO_2R^{11}$ or —N=N—$R^{14}$, wherein $R^{11}$ to $R^{14}$ has the meanings described above.

$R^{20}$ represents optionally substituted alkyl, in particular $C_1$-$C_{18}$-alkyl, preferably $C_1$-$C_4$-alkyl, optionally substituted cycloalkyl, in particular cyclohexyl or cyclopentyl, optionally substituted aralkyl, in particular phenyl- or naphthyl-$C_1$-$C_4$-alkyl, optionally substituted aryl, in particular phenyl or naphthyl, or an optionally substituted heterocyclic radical, in particular the radical of a five- or six-membered heterocyclic ring having 1, 2 or 3 heteroatoms from the series comprising O, N and S, onto which a benzene ring can optionally be fused. $R^{20}$ can be substituted by the substituents $Z_n$ described above (n=0, 1, 2 or 3), but wherein Z may not represent free hydroxyl or amino groups or primary amino groups. $R^{20}$ can furthermore also assume the meaning of G.

The carbanions are produced by addition of alkali metals in a suitable form or of organometallic compounds, such as methyl- or butyl-lithium, or of amide salts, such as lithiumdiisopropylamide, to G—$CH_2$—$R^{20}$.

The carbanion precursors G—CH$_2$—R$^{20}$ can also be of a nature such that the meaning of R$^{20}$ includes the possibility of bidentate carbon nucleophiles, such as G—CH$_2$—G$^1$—CH$_2$—G. G$^1$ here again represents carbanion-stabilizing radicals, such as

or —SO$_2$—.

Compounds of type VII can furthermore be prepared by reacting compounds of type II with organometallic alkyl derivatives, such as methyl- or butyllithium.

Compounds of the formula IX are prepared by reacting compounds of type V with elemental sulphur, sodium sulphide(hydrate), NaHs, hydrazine or a hydrazine derivative, such as, for example, hydrazodicarboxylic acid esters, if appropriate in the presence of a high-boiling solvent, such as ethylene glycol or diethylene glycol, at temperatures between 100° C. and 250° C., preferably between 120° C. and 200° C.

Compounds of the formula X are prepared by reacting compounds of type II with elemental sulphur, sodium sulphide hydrate, NaHs, hydrazine or a hydrazine derivative, if appropriate in the presence of a high-boiling solvent, at temperatures of 100° C. to 300° C., preferably between 150° C. and 250° C.

Compounds of type XI are prepared by reacting compounds of type II with urea or urea derivatives, such as monoalkyl-, monoaryl-, N,N'-dialkyl- or N,N'-diarylureas or thioureas, in inert solvents, such as toluene or xylenes, in the presence of acid-binding agents, such as alkali metal carbonates or high-boiling tertiary amines, at temperatures of 100° C. to 200° C., preferably 120° C. to 140° C. II can furthermore also be reacted in carbonate melts to give compounds of type XI.

Compounds of type XIII are prepared by reacting compounds of type II with the following bidentate or ambidentate nucleophiles:

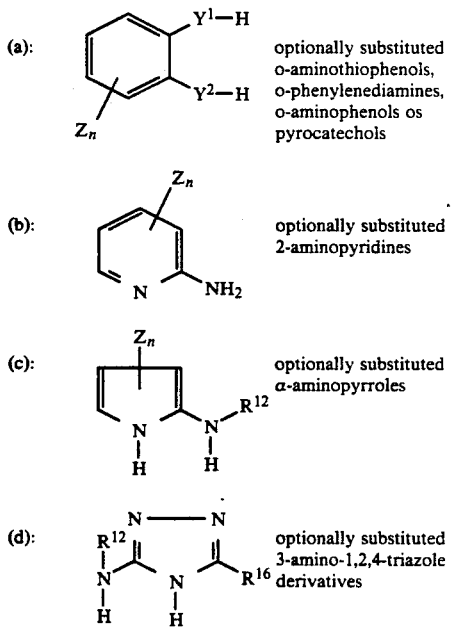

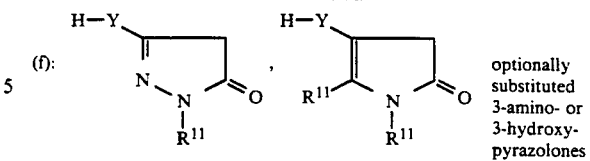

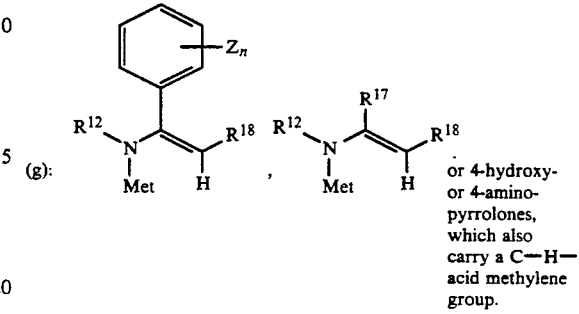

Alkali metal salts of optionally substituted aminocinnamonitriles, aminocinnamic acid esters, aminocrotonitriles or aminocrotonic acid esters in the presence of another acid-binding salt. Advantageously, for example, the disodium salts obtained directly in the synthesis of aminocinnamic acid nitriles are used (E. v. Meyer, J.pr.Ch. [2] 52, 110).

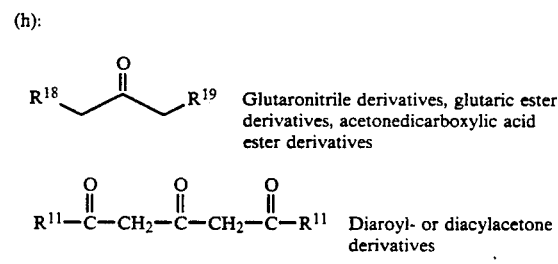

The reactions are carried out in high-boiling solvents, such as toluenes, xylenes or o-dichlorobenzene, if appropriate in the presence of acid-binding agents, such as alkali metal carbonates or tertiary amines, at temperatures between 100° C. and 250° C., preferably 140° C. and 200° C.

Compounds of formula XIII in which Y$^6$ represents —S—S— are prepared by reacting compounds of type II with sodium hydrogen sulphide solution in water-miscible solvents, such as alcohols or dimethylformamide, in the presence of oxygen at temperatures between 50° C. and 150° C, preferably between 80° C. and 100° C.

Compounds of type XIII having the bridging unit (e) are prepared by heating compounds of type XIII having the bridging unit (a), in which one of the radicals Y$^1$ or Y$^2$ represents sulphur, to temperatures between 200° C. and 300° C. in high-boiling inert solvents, such as biaryls or diphenyl ethers, sulphur atoms being eliminated.

Compounds XIII (e) can furthermore be prepared by heating compounds of type IV, where n=1 and

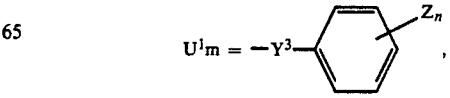

m=1, to temperatures above 110° C., if appropriate in the presence of a suitable catalyst, such as FeCl₃, and/or an acid-binding agent. $Y^3$ and $Z_n$ has the meanings described for formula Va.

Compounds of the type XVI are prepared by reacting compounds of type XIII with elemental sulphur, sodium sulphide hydrate, NaHS, hydrazine or hydrazine derivatives, if appropriate in high-boiling solvents, such as ethylene glycol or diethylene glycol, if appropriate in the presence of acid-binding agents, at temperatures between 150° C. and 300° C., preferably between 200° C. and 250° C. In some cases, the reaction must be carried out under increased pressure.

Substances of the formula II are useful intermediate products for the preparation of dyestuffs, pigments, photoconductor substances or substances for organic conductors.

The substances of type V are soluble dyestuffs for bulk dyeing of plastics in yellow to violet shades. Plastics which may be mentioned are, for example, polystyrene, polycarbonates, polyurethanes, polyamides or polyolefins. The dyeings are distinguished by a high brilliance and good heat stability.

Substances the formula VI are blue to green pigments, those of the formula IV are yellow to red pigments or dyestuffs, those of the formulae XI and XIII are red-violet to blue pigments and those of the formula XVI are blue to green pigments.

The compounds of the formulae VI, IX, XI, XIII and XVI are obtained in a form suitable for use as pigments or can be converted into the suitable form by after-treatment processes which are known per se, for example by dissolving or swelling in strong inorganic acids, such as sulphuric acid, and pouring the mixture onto ice. Fine division can also be achieved by grinding with or without grinding auxiliaries, such as inorganic salts or sand, if appropriate in the presence of solvents, such as toluene, xylene, dichlorobenzene or N-methylpyrrolidone. The tinctorial strength and transparency of the pigment can be influenced by varying the after-treatment.

Because of their fastness to light and migration, the compounds of the formula VI, IX, XI, XIII or XVI are suitable for widely varying pigment applications. They can thus be used for the preparation of very fast pigmented systems as a mixture with other substances, formulations, paints, printing inks, coloured paper and coloured macromolecular substances. Mixture with other substances can be understood as meaning, for example, those with inorganic white pigments, such as titanium dioxide (rutile), or with cement. Formulations are, for example, flush pastes with organic liquids or pastes and fine pastes with water, dispersing agents and if appropriate preservatives. The term paint represents, for example, surface coatings which dry by physical means and oxidation, stoving enamels, reactive varnishes, two-component varnishes, emulsion paints for weatherproof coatings and distempers.

Printing inks are to be understood as those for printing paper, textiles and sheet metal. The macromolecular substances can be of natural origin, such as rubber, obtained by chemical modification, such as acetylcellulose, cellulosebutyrate or viscose, or synthetically produced, such as polymers, polyaddition products and polycondensates. Substances which may be mentioned are plastic compositions, such as polyvinyl chloride, polyvinyl acetate, polyvinyl propionate, polyolefins, for example polyethylene, or polyamides, high molecular weight polyamides, polymers and copolymers of acrylic esters, methacrylic esters, acrylonitrile, acrylamide, butadiene and styrene, as well as polyurethanes and polycarbonates. The substances pigmented with the products claimed can also be in any desired form.

EXAMPLE 1

40 g of the compound XVIII are mixed with 240 g of PCl₅ and the mixture is stirred on an oil bath at a bath temperature of 150° C. to 160° C. for 24 hours. About 60 ml of POCl₃ are gradually distilled off in the course of the reaction, and after 24 hours the POCl₃ formed is distilled off as completely as possible. The orange-coloured solid residue, which still contains excess PCl₅, is poured onto 2 l of ice-water and the product is filtered off with suction and dried in vacuo.

52 g of a compound of the formula

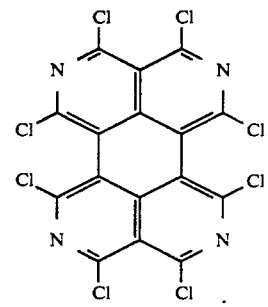

which can be further purified if necessary, by recrystallization from nitrobenzene with the addition of PCl₅, are obtained.

IR data: 1535, 1292, 1240, 1183, 893 cm⁻¹

UV VIS data: λ=452, 480 nm (19 300)

¹³C-NMR data (solid): δ=117.6, 130.11, 132.3, 145.6, 155.3 ppm.

EXAMPLE 2

5.0 g of the compound from Example 1 are stirred together with 4.6 g of phenol and 5.7 g of potassium carbonate in 10 ml of o-dichlorobenzene at 140° C. to 150° C. for 1.5 hours. After cooling, the product is filtered off with suction and the suction filter cake is suspended in water and filtered off with suction again. 6.1 g of a brilliant yellow crystalline powder of the formula

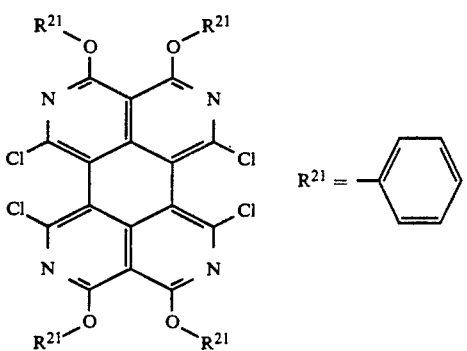

are obtained.

IR data: 3080, 3050, 1570, 1520, 1490, 1390, 1290, 1240, 1205, 940, 810, 750, 690 cm⁻¹.

UV/VIS data: $\lambda_{max}$=465, 440 nm (ε=24 600)

The dyestuffs listed in the following table can be obtained by a similar procedure to that above in Example 2.

| Example number | R²¹ | UV/VIS data |
|---|---|---|
| 3 | (4-chlorophenyl) | λ = 466, 440 nm |
| 4 | (3-chlorophenyl) | λ = 465, 435 nm |
| 5 | (3,5-dimethylphenyl) | λ = 468, 441 nm, ε = 24, 150 |
| 6 | —CH₃ | λ = 452, 427 nm |
| 7 | —S—(phenyl) | λ = 536 nm |

EXAMPLE 8

11.0 g of the compound from Example 1 are boiled under reflux together with 8.5 g of triethylamine and 3.0 g of α-aminopyridine in 100 ml of toluene for 40 minutes. After cooling, the solid is filtered off with suction and washed abundantly with ethanol. 10 g of a red-orange dyestuff of the formula

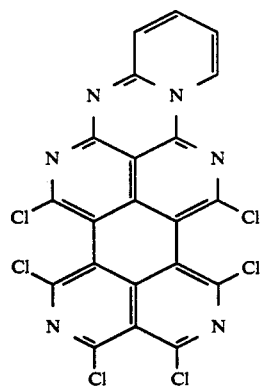

are obtained.

IR data: 1615, 1590, 1490, 1445, 1360, 1330, 1230, 1190, 1155, 1090cm⁻¹

UV VIS data: $\lambda_{max}$=547 nm (ε=29 000)

EXAMPLE 9

3.0 g of the compound from Example 1 are stirred in 20 ml of aniline at 150° to 160° C. for 90 minutes. The mixture is then cooled and stirred into ethanol and the solid is filtered off with suction. The suction filter cake is stirred in water, filtered off with suction again and dried. 3.5 g of a compound which, in one of its tautomeric forms, corresponds to the formula

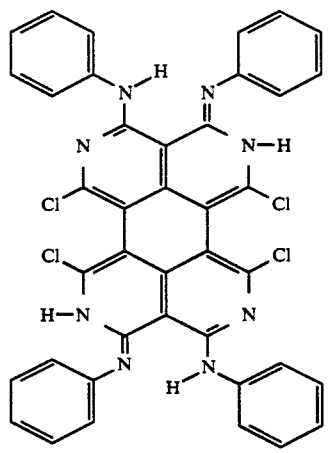

are obtained.

IR data: 1570, 1500, 1450, 1325, 1190, 940 cm⁻¹
UV VIS data: $\lambda_{max}$=547 nm (ε=39 300)

EXAMPLE 10

10 g of the compound from Example 1 are boiled under reflux together with 5.2 g of o-aminothiophenol and 8.4 g of triethylamine in 100 ml of toluene for 4 hours. After cooling, the solid is filtered off with suction and the suction filter cake is washed with water and methanol. 10 g of a red-violet pigment of the formula

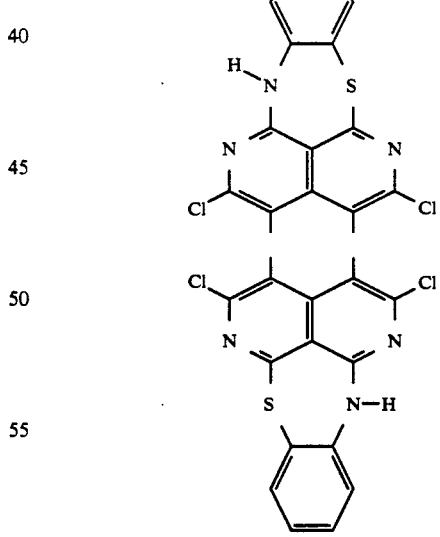

and its $C_{2v}$ isomer are obtained.

IR data: 1555, 1485, 1430, 1325, 1278, 1189, 760 cm⁻¹
UV VIS data: $\lambda_{max}$=560 nm (ε=20 200)

EXAMPLE 11

10 g of the compound from Example 10 are boiled under reflux in 100 ml of o-dichlorobenzene for 5 hours. 8 g of a violet pigment of the formula

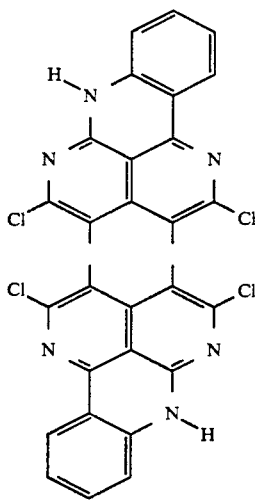

and a $C_{2\nu}$ isomer or a mixture of the two isomers are obtained.

EXAMPLES 12, 13

If the procedure is according to the information in Example 10 and o-aminophenol (Example 12) or o-phenylenediamine (Example 13) is employed instead of o-aminothiophenol, red-violet (Example 13, $\lambda_{max}=532$, 502 nm) or orange-red (Example 12, $\lambda_{max}=528$ nm) pigments having a structure analogous to that shown in Example 10 are obtained.

EXAMPLE 14

5 ml of a 30 % strength aqueous NaHS solution are added dropwise to 2.0 g of the compound from Example 1 in 20 ml of diethylene glycol. The mixture is then stirred at 120° C. for 90 minutes. It is poured onto 100 ml of water and acidified with HCl and the solid is filtered off with suction. 1.9 g of a soluble, violet dyestuff of the formula

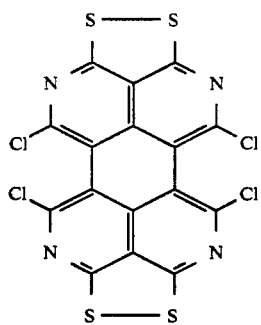

MS data: m+ =516 ($^{35}Cl_4$)
UV VIS data: $\lambda_{max}=557$, 519 nm

EXAMPLE 15

13.2 9 of the compound from Example 1, 13.2 g of $Na_2S \times 3H_2O$ and 53 g of sulphur are mixed thoroughly and the mixture is heated to 250° C. (internal temperature) and stirred at this temperature for 2 hours. After this period of time, the mixture is allowed to cool to an internal temperature of 100° C., 100 ml of toluene are added and this mixture is poured into 300 ml of hot toluene. The solid is filtered off hot with suction. The suction filter cake is ground in a mortar, boiled up again in 300 ml of toluene and filtered off with suction.

The suction filter cake is suspended in 400 ml of water and the suspension is stirred vigorously for 12 hours, with oxygen access. After filtration with suction, washing with water and drying, 11 g of a green pigment of the formula

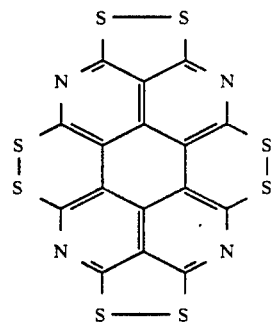

are obtained.

MS: m+ =504 (100%; $S_8$-mass)

IR data: 1580, 1545, 1480, 1376, 1350, 1310, 1230, 1192, 890 cm$^{-1}$.

EXAMPLE 16

5 g of the compound from Example 1, 9 ml of triethylamine and 1.7 g of urea are stirred in 50 ml of xylene at 150° C. for 5 hours. The solid is filtered off with suction, washed with methanol and water and dried. 3.5 g of a red-violet pigment of the formula

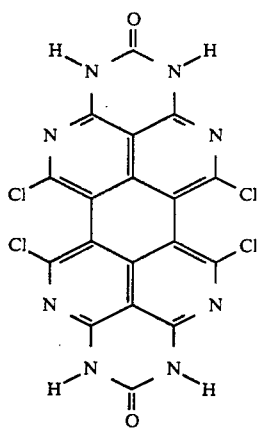

are obtained
UV VIS data: $\lambda_{max}=545$ nm

EXAMPLES 17 TO 19

The procedure is as described in Example 16, but instead of urea, the substituted representatives N,N'-dimethylurea, phenylurea and N,N'-diphenylurea are employed. In each case red-violet pigments having a structure analogous to Example 16 are isolated.

EXAMPLE 20

3 g of the compound from Example 1 and 7 g of a disodium salt of the compound

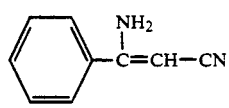 XX prepared from benzonitrile, acetonitrile and sodium in accordance with J. Pr. Ch. [2] 52, 110 are boiled under reflux in 30 ml of toluene for 15 hours. After addition of 5 ml glacial acetic acid, the solid is filtered off with suction and washed with water and methanol. 1.3 g of a red-violet pigment of the formula

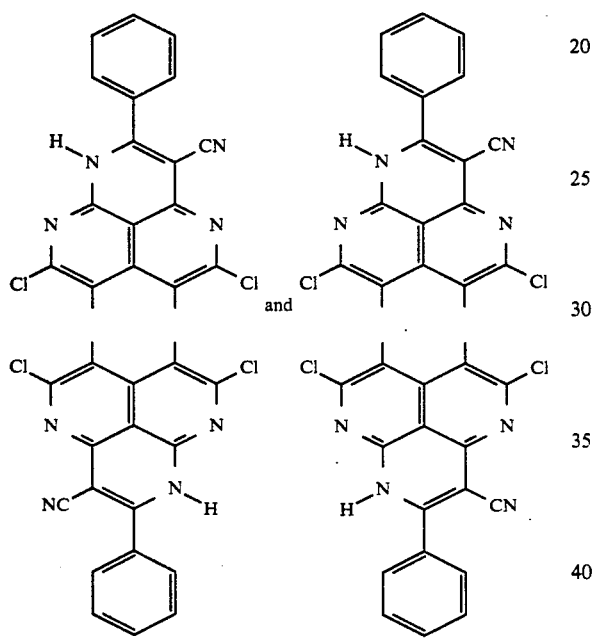

or a mixture of the possible isomers, are obtained.

IR data: 2230, 1600, 1510, 1320, 1190, 700 cm$^{-1}$.

EXAMPLE 21

2 g of the compound from Example 1 are boiled under reflux together with 1.6 g of the pyrazolone

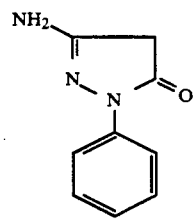 XXI and 3 ml of triethylamine in 40 ml of toluene for 4 hours. The solid is then filtered off with suction and the suction filter cake is washed with water and methanol. 2.4 g of a red-violet pigment of the formula

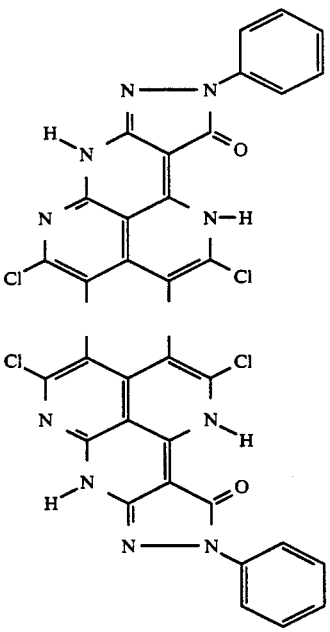

and or a mixture of the possible isomers, are obtained.

EXAMPLE 22

3 g of the compound from Example 1 are stirred in 30 ml of hydrazine hydrate at 80° C. for 1 hour. The solid is then filtered off with suction and washed with water. 2.2 g of a brown-red pigment of the probable structure

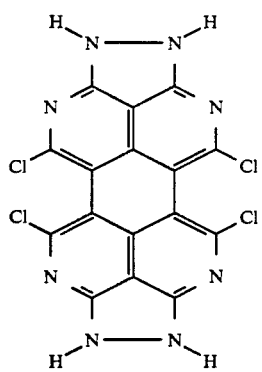

are obtained.

EXAMPLE 23 (USE EXAMPLE)

4 g of finely ground pigment according to Example 15 are dispersed in 92 g of a stoving enamel of the following composition:
33% of alkyd resin
15% of melamine resin
5% of glycol monomethyl ether
34% of xylene
13% of butanol.

Possible alkyd resins are products based on synthetic and vegetable fatty acids, such as coconut oil, castor oil, hydrogenated castor oil, linseed oil and the like. Instead of melamine resins, urea resins can be used. After the dispersion has taken place, the pigmented enamel is applied to foils of paper, glass, plastic or metal and stoved at 130° C. for 30 minutes. The surface coatings have very good resistance to light and weathering and good fastness to over-lacquering.

This stoving enamel is brushed onto white paper and stoved at 130° C., and shows a green colour shade.

I claim:

1. A heterocyclic compound of the formula

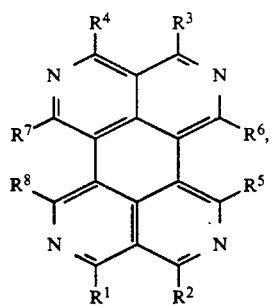

wherein
$R^1$ to $R^8$ denote H, halogen, alkyl, cycloalkyl, aralkyl, aryl, a heterocyclic radical, $NR^9R^{10}$, $OR^9$ or $SR^9$, wherein
$R^9$ and $R^{10}$ denote H, alkyl, cycloalkyl, aralkyl, aryl or a heterocyclic radical,
or wherein the radicals $R^1$ and $R^2$, and $R^3$ and $R^4$, $R^5$ and $R^6$, and $R^7$ and $R^8$ together can form components of fused-on carbocyclic or heterocyclic 5-, 6- or 7-membered rings.

2. A compound of claim 1, of the formula

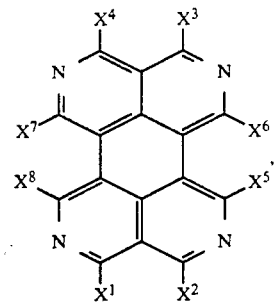

wherein $X^1$ to $X^8$ can be identical or different and represent Br, Cl or F.

3. A compound of claim 2, where $X^1$ to $X^8$ = chlorine.

4. A compound of claim 1, of the formula

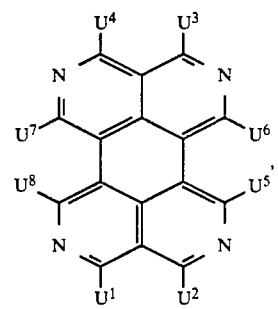

wherein $U^1$ to $U^8$ can be identical or different from one another and represent $OR^9$, $SR^9$ or $NR^9R^{10}$.

5. A compound of claim 1, of the formula

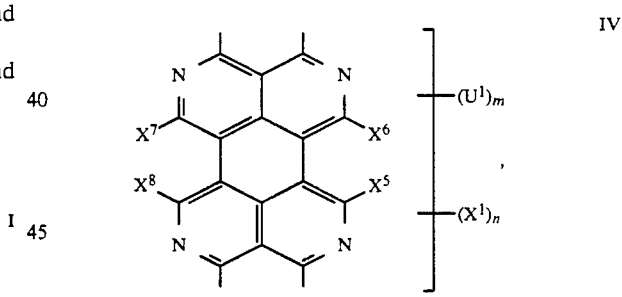

wherein
$U^1$ represents identical or different radicals $OR^9$, $SR^9$ or $NR^9R^{10}$; $X^1$ to $X^8$ are identical or different and represent F, Cl or Br and m and n denote 1–4, wherein $m+n=4$.

6. A compound of claim 5, of the formula

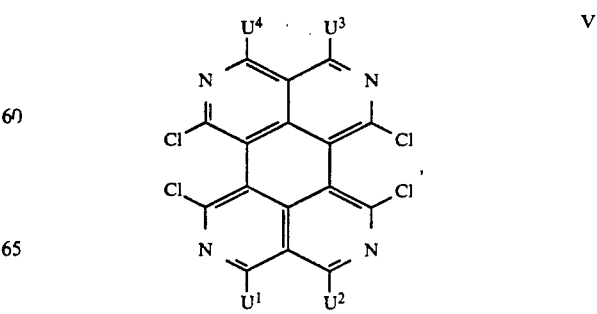

wherein $U^1$-$U^4$ have the meaning as given in claim 4.

7. A compound of claim 6, where $U^1$-$U^4$ independently of one another

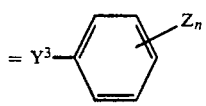

where
$Y^3$=O, S or NH,
n=0, 1, 2, or 3 and
Z=$OR^{11}$, $NR^{12}R^{13}$, $SR^{11}$, $COOR^{11}$, CN, Br, Cl, F, $CONR^{12}R^{13}$, $SO_2R^{11}$, $SO_2OR^{11}$, $SO_2NR^{12}R^{13}$, —N=N—$R^{14}$, $R^{15}$, $OCOR^{11}$, $NR^{12}COR^{11}$ or $COR^{11}$, wherein
$R^{11}$, $R^{12}$ and $R^{13}$ designate hydrogen, optionally substituted alkyl, optionally substituted cycloalkyl, optionally substituted aralkyl, optionally substituted aryl, or an optionally substituted heterocyclic radical, wherein $R^{12}$ and $R^{13}$ together, including the N atom, can also form a 5- or 6-membered heterocyclic ring:

$R^{14}$ designates the radical of a coupling component, of the benzene, naphthalene, acetoacetatearylide, pyrazole or pyridone series, or a phenyl radical which is optionally substituted by Cl, Br, F, $C_1$-$C_{18}$-alkyl, preferably $C_1$-$C_4$-alkyl, or $C_1$-$C_{18}$-alkoxy, preferably $C_1$-$C_4$-alkoxy;

$R^{15}$ designates optionally substituted alkyl, or optionally substituted cycloalkyl.

8. A compound of claim 1, of the formula

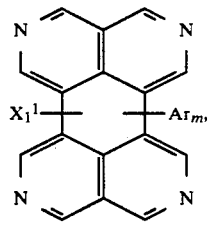

VI wherein
$X^1$=F, Cl or Br, Ar=an aromatic or heterocyclic radical, l and m=0–8, wherein l+m=8, and adjacent groups Ar can also be components of a single fused aromatic system.

9. A compound of claim 2, of the formula

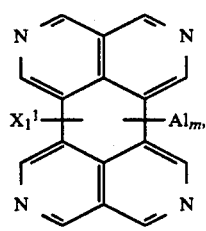

VII wherein
$X_1$=F, Cl or Br, Al=an optionally substituted alkyl, cycloalkyl or aralkyl radical and l and m=0–8, wherein l+m=8.

10. A compound of the formula

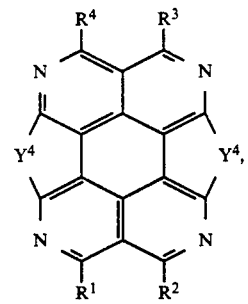

VIII wherein —$Y^4$— represents —S—, —S—S—, —N=N—,

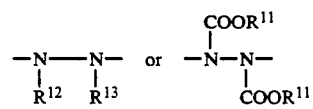

and $R^{11}$ to $R^{14}$ have the meaning given in claim 7.

11. A compound of claim 1 of the formula

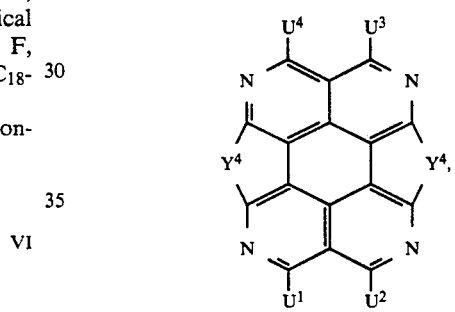

IX wherein $U^1$-$U^4$ have the meaning given in claim 4.

12. A compound of claim 1, of the formula

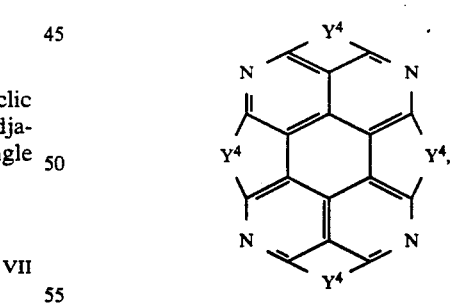

X wherein
—$Y^4$— represents —S—, —S—S—, —N=N—,

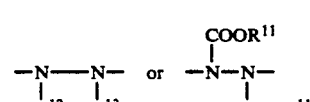

and wherein —$Y^4$— may not be the constituent of a four-membered ring.

13. A compound of claim 1, of the formula

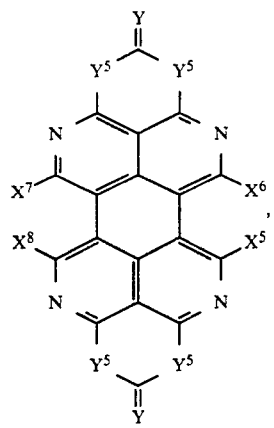

wherein
$Y^5 = O$ or $NR^{12}$, $Y = O$, S or $NR^{12}$ wherein $R^{12}$ designates hydrogen, optionally substituted alkyl, optionally substituted cycloalkyl, optionally substituted aralkyl, optionally substituted aryl or an optionally substituted heterocyclic radical and $X^5-X^8 = F$, Cl or Br.

14. A compound of claim 13, where $X^5-X^8 = Cl$ and $Y^5 = NH$.

15. A compound of claim 1, of the formula

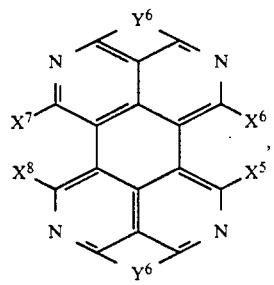

wherein $X^5$ to $X^8 = F$, Cl or Br and —$Y^6$— represents the following bridging units:

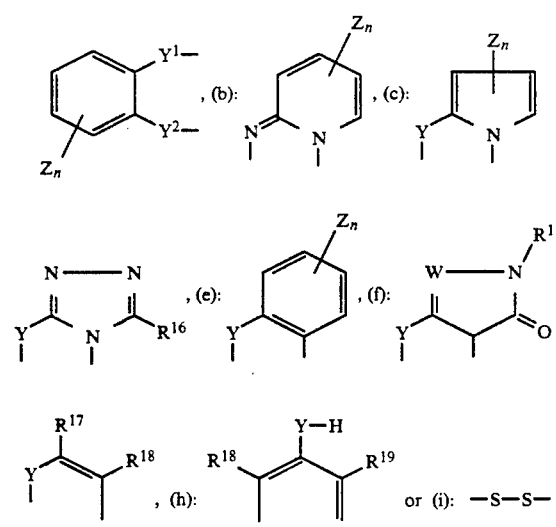

wherein
$W = N$ or $C-R^{11}$,

Z and $R^{11}-R^{13}$ have the meaning given in claim 7,

Y, $Y^1$ and $Y^2 = O$, S, $NR^{12}$ or $NR^{13}$, $R^{16} = H$ or Z, $R^{17}$ = optionally substituted aryl or hetaryl, $R^{18} = CN$, $COOR^{11}$ or $COR^{11}$ and $R^{19} = CN$, $COOR^{11}$, $COR^{11}$, $SO_2R^{11}$ or $CONR^{12}R^{13}$.

16. A compound of claim 15, of the formulae

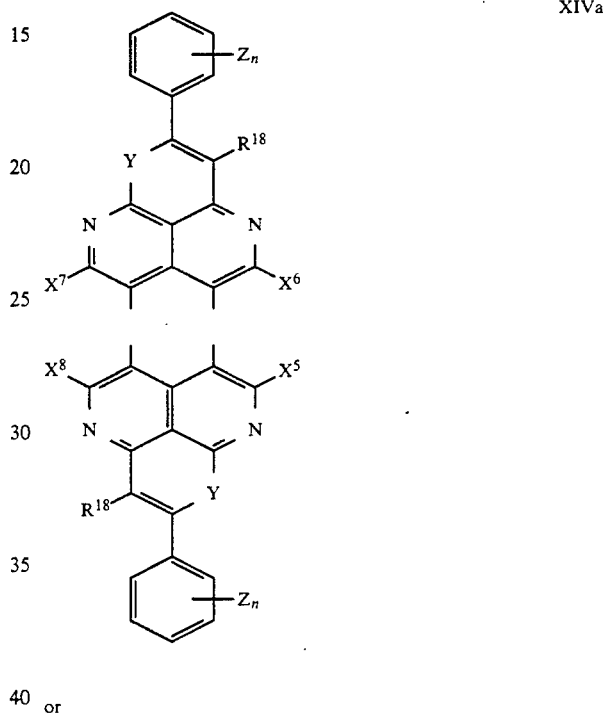

or

-continued
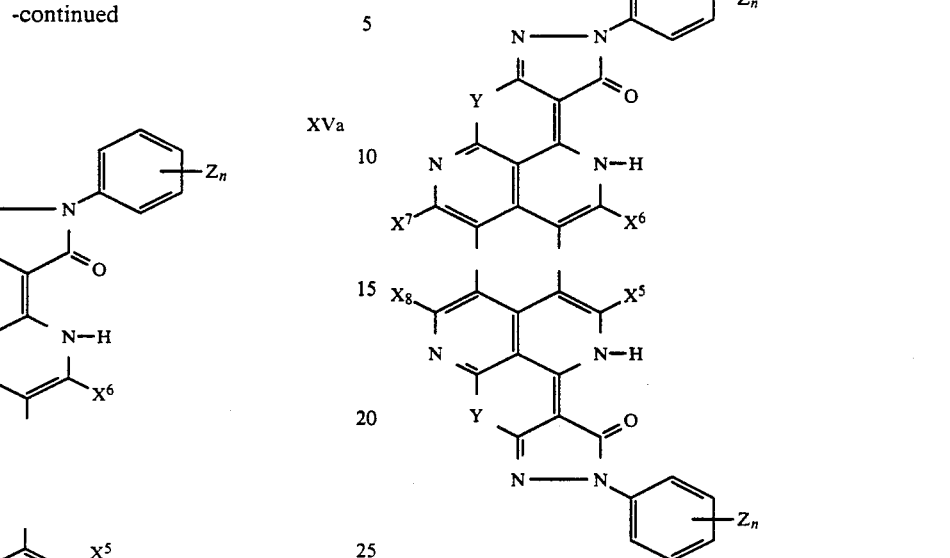
XVa
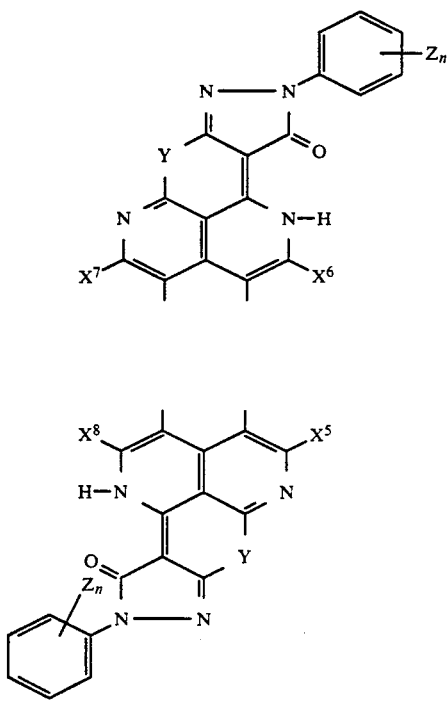
or
XVb
17. A compound of claim 1, of the formula
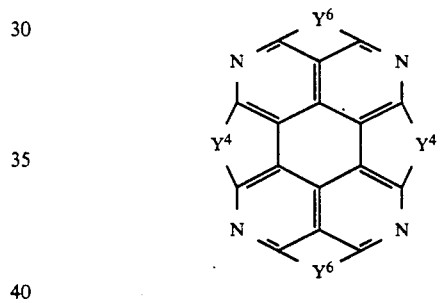
wherein
Y$^4$ has the meaning given in claim 10 and
Y$^6$ has the meaning give in claim 15.
18. Process for dyeing a substrate with a dyestuff or a pigment wherein as dyestuff or pigment a heterocyclic compound according to claim 1 is used.
* * * * *